United States Patent [19]

Crivello et al.

[11] 4,329,300

[45] May 11, 1982

[54] METHOD FOR MAKING DIARYLIODONIUM POLYHALOMETALLOID SALTS

[75] Inventors: James V. Crivello, Clifton Park; Julia H. Lam, Schenectady, both of N.Y.

[73] Assignee: General Electric Company, Schenectady, N.Y.

[21] Appl. No.: 163,725

[22] Filed: Jun. 27, 1980

[51] Int. Cl.³ .................... C07F 9/68; C07F 9/92; C07F 9/06
[52] U.S. Cl. ................... 260/440; 260/446; 568/17
[58] Field of Search ............ 260/440, 441; 568/17

[56] References Cited

U.S. PATENT DOCUMENTS 3,981,897  9/1976  Crivello ........................ 260/440
4,058,400 11/1977  Crivello ........................ 260/440 X
4,151,175  4/1979  Crivello ........................ 260/440 X
4,219,654  8/1980  Crivello ........................ 260/440 X

*Primary Examiner*—Helen M. S. Sneed
*Attorney, Agent, or Firm*—William A. Teoli; James C. Davis, Jr.

[57] ABSTRACT

A method is provided for making certain diaryliodonium salt photoinitiators, based on the initial formation of diaryliodonium perchlorate which is formed from a diaryliodonium bisulfate precursor. The diaryliodonium perchlorate is then reacted with a counter ion source, such as an alkali metal hexafluoro metalloid salt, to produce the desired diaryliodonium salt, which can be used as a photoinitiator. The iodonium salt photoinitiators made by the method of the present invention can be used to effect the cure of a variety of cationically polymerizable organic materials, such as epoxy resins.

5 Claims, No Drawings

METHOD FOR MAKING DIARYLIODONIUM POLYHALOMETALLOID SALTS

BACKGROUND OF THE INVENTION

The present invention relates to a method for making diaryliodonium polyhalometalloid salts by reacting a diaryliodonium perchlorate with an alkali metal polyhalometalloid salt.

Prior to the present invention, as shown by U.S. Pat. No. 3,981,897, assigned to the same assignee as the present invention, diaryliodonium polyhalometalloid salts were made by effecting reaction between diaryliodonium bisulfate salt and alkali metal polyhalometalloid salt. Improved results were achieved in Crivello et al. U.S. Pat. No. 4,151,175 employing methylene chloride as a solvent in the reaction in place of acetic acid during the formation of the diaryliodonium bisulfate salt. Although satisfactory results are achieved by the aforementioned methods, a considerable excess of the polyhalometalloid salt, such as potassium hexafluoroarsenate is required in the diaryliodonium bisulfate salt reaction mixture to achieve optimum yields of the diaryliodonium polyhalo metalloid salts. As a result, the diaryliodonium bisulfate route to diaryliodonium polyhalo metalloid salts is economically less attractive because of the significant losses of the polyhalometalloid salts.

The present invention is based on the discovery that diaryliodonium polyhalometalloid salts of the formula, $$[(R)_a(R^1)_bI]^+[MX_c]^- \tag{1}$$

can be made by effecting reaction between a diaryliodonium perchlorate and a polyhalometalloid alkali metal salt in the presence of an organic solvent to provide quantitative yields ity of utilizing excess amounts of polyhalometalloid salts, where R is a monovalent aromatic organic radical, $R^1$ is a divalent aromatic organic radical, X is a halogen radical, such as I, Br, Cl, F, etc., M is a Group IIIb metal or Group Va metalloid, a is a whole number equal to 0 or 2, b is a whole number equal to 0 or 1, the sum of a+b is equal to 1 or 2 and c is an integer equal to 4-6 inclsuive.

STATEMENT OF THE INVENTION

In the method for making diaryliodonium salts of formula (1), based on a metathesis between a diaryliodonium bisulfate salt of the formula, $$[(R)_a(R^1)_bI]^+HSO_4^- \tag{2}$$

and a polyhalometal or metalloid salt of the formula, $$YMX_c, \tag{3}$$

referred to hereinafter as "polyhalometalloid salt", whereby a stoichiometric excess of the polyhalometalloid salt is required to provide quantitative yields of the diaryliodonium salts of formula (1), the improvement which comprises, effecting the metathesis reaction between substantially equal molar amounts of the polyhalometalloid salt and a diaryliodonium perchlorate salt of the formula, $$[(R)_a(R^1)_bI^+ClO_4^-, \tag{4}$$

whereby a quantitative yield of the diaryliodonium salt of formula (1) is achieved, where Y is an element selected from the class consisting of hydrogen, alkali metals and alkaline earth metals, and R, $R^1$, M, X, a and b are as previously defined.

Radicals included by R can be the same or different aromatic carbocyclic or heterocyclic radicals having from 6-20 carbon atoms, which can be substituted with from 1-5 monovalent radicals selected from $C_{(1-8)}$ alkoxy, $C_{(1-8)}$ alkyl, nitro, chloro, etc., R is more particularly, phenyl, chlorophenyl, nitrophenyl, methoxyphenyl, pyridyl, etc. Ralicals included by $R^1$ are divalent radicals, such as

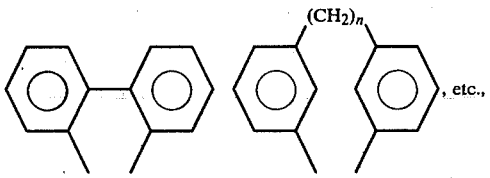

where n is an integer equal to 1 to 4 inclusive.

The aryliodonium perchlorate salt of formula (4) is well known as shown by K. A. Hofmann, et cl, Berichte, 2624 (1910). These salts can be made by effecting reaction between substantially equal molar amounts of the diaryliodonium bisulfate salt of formula (2) in an aqueous solution with an alkali metal perchlorate. The resulting diaryliodonium perchlorate salt is insoluble in water and it can be recovered by filtration. The diaryliodonium perchlorate salt can then be dissolved in a suitable organic solvent and metathesis can be effected at a temperature of 0° C. to 100° C. with equal molar amounts of polyhalometalloid salt. Organic solvents which can be used are ketones, alcohols, nitrohydrocarbons, chlorinated aromatic hydrocarbon, etc. Suitable polyhalometalloid salts of formula (3) are, for example, $NaBF_4$, $KAsF_6$, $KSbF_6$, $NaPF_6$, $NaSbCl_6$, $Ca(PF_6)_2$, $HPF_6$, $Pb(SbF_6)_2$, $Ba(AsF_6)_2$, etc.

In order that those skilled in the art will be better able to practice the invention, the following examples are given by way of illustration and not by way of limitation. All parts are by weight.

EXAMPLE 1

There was slowly added at minus 10° C. about 25 parts of concentrated sulfuric acid to a mixture of 25 parts of potassium iodate, 32 parts of benzene, 50 parts of acetic anhydride and 60 parts of methylene chloride. The mixture was stirred for 4 hours and maintained at a temperature of minus 5° C. and then allowed to rise slowly to 25° C. The mixture was then stirred for an additional 12 hours and then there was slowly added about 100 parts of water. The lower methylene chloride layer was removed from the reaction mixture and discarded. There was added 14.3 parts of sodium perchlorate to the aqueous layer resulting in precipitate. Based on method of preparation, the precipitate was diphenyliodonium perchlorate. The diphenyliodonium perchlorate was then dried.

A mixture of 2 parts of diphenyliodonium perchlorate, 1.2 part of potassium hexafluoroarsenate and about 60 parts of methylethyl ketone was stirred for 1 hour. The mixture was then filtered to remove precipitated potassium perchlorate. Evaporation of the methylethyl ketone resulted in a crystalline product having a melting point of 123°–125° C. Based on method of preparation, the product was diphenyliodonium hexafluoroarsenate which was obtained at a 96% yield.

EXAMPLE 2

A mixture of 4 parts of diphenyliodonium perchlorate, 1.95 parts of potassium hexafluorophosphate and about 90 parts of methylethyl ketone was stirred for 1 hour at room temperature and then filtered to remove precipitated potassium perchlorate. The remaining solution was then evaporated to dryness resulting in 4 parts of a solid having a melting point of 127°–131° C. Based on method of preparation, there was obtained a 94% yield of diphenyliodonium hexafluorophosphate.

EXAMPLE 3

A mixture of 4 parts of diphenyliodonium perchlorate and 2.8 parts of potassium hexafluoroantimonate and 100 parts of methanol was stirred for 1 hour at 25° C. The resulting mixture was then filtered and the methanol solution evaporated to produce a solid having a melting point of 77°–87° C. Based on method of preparation there was obtained an 86.1% yield of diphenyliodonium hexafluoroantimonate.

Although the above examples are directed to only a few of the very many variables in the practice of the method of the present invention, it should be understood that the present invention is directed to a much broader variety of diaryliodonium polyhalometalloid salts, as shown by formula (1), resulting from the reaction of a polyhalometalloid salt of formula (3) and a diaryliodonium perchlorate salt of formula (4).

What we claim as new and desire to secure by Letters Patent of the United States is:

1. In the method for making diaryliodonium salts of the formula, $$[(R)_a(R^1)_bI]^+[MX_c]^-,$$

based on a metathesis between a diaryliodonium bisulfate salt of the formula, $$[(R)_a(R^1)_bI]^+HSO_4^-,$$

and a polyhalometalloid salt of the formula, $$YMX_c,$$

whereby a stoichiometric excess of the polyhalometalloid salt is required to provide quantitative yields of the diaryliodonium salts, the improvement which comprises, effecting the metathesis reaction between substantially equal molar amounts of the polyhalometalloid salt and a diaryliodonium perchlorate salt of the formula, $$[(R)_a(R^1)_bI]ClO_4^-,$$

to achieve quantitative yields of the diaryliodonium salts, where R is a monovalent aromatic organic radical, $R^1$ is a divalent aromatic organic radical, Y is an element selected from the class consisting of hydrogen, alkali metals and alkaline earth metals, X is a halogen radical, M is a Group IIIb metal or Group Va metalloid, a is a whole number equal to 0 or 2, b is a whole number equal to 0 or 1, the sum of a+b is equal to 1 or 2 and c is an integer equal to 4–6 inclusive.

2. A method in accordance with claim 1, where the diaryliodonium salt is a diphenyliodonium salt.

3. A method in accordance with claim 1, where the diaryliodonium salt is diphenyliodonium hexafluoroarsenate.

4. A method in accordance with claim 1, where the diaryliodonium salt is diphenyliodonium hexafluorophosphate.

5. A method in accordance with claim 1, where the diaryliodonium salt is diphenyliodonium hexafluoroantimonate.

* * * * *